United States Patent [19]

Hewawasam et al.

[11] Patent Number: 5,208,237
[45] Date of Patent: May 4, 1993

[54] 7-OXYPROPYLSULFONAMIDO-IMIDAZO[4,5-B]QUINOLIN-2-ONES

[75] Inventors: Piyasena Hewawasam, Middletown; Nicholas A. Meanwell, East Hampton, both of Conn.

[73] Assignee: Bristol-Meyers Squibb Company, New York, N.Y.

[21] Appl. No.: 862,879

[22] Filed: Apr. 3, 1992

[51] Int. Cl.$^5$ .................. A61K 31/495; C07D 487/04
[52] U.S. Cl. ..................................... 514/254; 514/253; 544/361
[58] Field of Search ................. 544/361; 514/253, 254

[56] References Cited

U.S. PATENT DOCUMENTS

| | | | |
|---|---|---|---|
| 3,932,407 | 1/1976 | Beverung, Jr. et al. | 514/253 |
| 4,256,748 | 3/1981 | Chodnekar et al. | 514/253 |
| 4,490,371 | 12/1984 | Jones et al. | 514/253 |
| 4,668,686 | 5/1987 | Meanwell et al. | 514/253 |
| 4,701,459 | 10/1987 | Meanwell et al. | 544/361 |
| 4,775,674 | 10/1988 | Meanwell et al. | 544/361 |
| 4,943,573 | 7/1990 | Meanwell | 544/361 |

FOREIGN PATENT DOCUMENTS 153152  8/1985  European Pat. Off. .

OTHER PUBLICATIONS

S. Seiler et al., "Imidazoquinoline Derivatives: Potent Inhibitors of Platelet cAMP Phosphodiesterase which Elevate cAMP Levels and Activate Protein Kinase in Platelets," Throm. Res., 62: 31-42 (1991).
Kozak, et al., Bull. Intern. Acad. Polanaise, 1930A: 432-438 (Chem. Abs. 25, 5400).
J. S. Fleming, et al., New Drugs Annual: Cardiovascular Drugs, Raven Press, 277-294, NY (1983).
J. S. Fleming, J. O. Buchanan, S. M. Seiler, and N. A. Meanwell, "Antithrombotic Activity of BMY 43351, a New Imidazoquinoline with Enhanced Aqueous Solubility," Thromb. Res., 63, 145-155 (1991).

Primary Examiner—Cecilia Tsang
Attorney, Agent, or Firm—Michelle A. Kaye

[57] ABSTRACT

A novel series of 1,3-dihydro-2H-imidazo[4,5-b]quinolin-2-ones having enhanced water solubility bioavailability and metabolic stability is disclosed in the Formula I

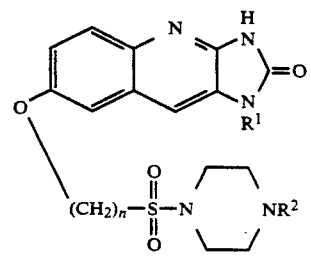

wherein
R$^1$ is H, or C$_1$-C$_4$ lower alkyl;
R$^2$ is H, (CH$_2$)$_m$R$^3$; benzoxazol-2yl, or benzothiazol2-yl;
R$^3$ is C$_1$-C$_8$ alkyl, C$_4$-C$_8$ cycloalkyl, or substituted or unsubstituted phenyl, wherein the substituents are halogen, alkoxy or trifluoromethyl;
m is an integer of 1-3; and
n is an integer of 1-5;

or pharmaceutically acceptable salt thereof.

The compounds are useful as inhibitors of ADP-induced blood platelet aggregation in human platelet-rich plasma.

17 Claims, No Drawings

7-OXYPROPYLSULFONAMIDO-IMIDAZO[4,5-B]QUINOLIN-2-ONES

BACKGROUND OF THE INVENTION

1. Field of the Invention

This invention relates to a new class of selective and potent inhibitors of platelet cyclic AMP phosphodiesterase is described. In particular, this invention relates to a series of new sulfonylpiperazine derivatives of imidazo[4,5-b]quinolin-2-one which are useful as inhibitors of ADP-induced aggregation of human blood plateletes in platelet-rich-plasma.

2. Description of the Art

Platelet aggregation is considered part of a complex physiological mechanism for formation of a thrombus in the vascular system. Thromboembolic phenomena, i.e., the formation of thrombi, are involved in hemostasis and a number of diseased states in mammals including thrombophlebitis, phlebothrombosis, cerebral thrombosis, coronary thrombosis and retinal vessel thrombosis. An increase in propensity for platelet aggregation, sometimes referred to as platelet adhesiveness, is observed following parturition, surgical operations such as coronary artery bypass surgery, organ transplant, angioplasty, prosthetic heart valve implants to name a few; and in ischemic heart disease, atherosclerosis, multiple sclerosis, intracranial tumors, thromboembolism, and hyperlipemia (A. Poplawski, et al, *J. Atherosclerosis Research*, 8: 721 (1968)).

The imidazo[4,5-b]quinolin-2-one derivatives have been identified as potent inhibitors of human blood platelet cAMP phosphodiesterase (PDE) and in vitro aggregation induced by ADP and collagen (Seiler et al., *Thromb. Res.*, 62, 31–42 (1991)).

The heterocycle "2,3-dihydro-2-oxo-1H-imidazo[4,5-b]quinoline" of the formula (I), alternately referred to as 1,3-dihydro-2H-imidazo[4,5-b]quinolin-2-one, was described by Kozak, et al, *Bull. Intern. Acad. Polanaise*, 1930A, 432–438 (Chem. Abs. 25, 5400)

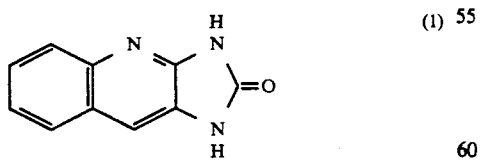

Derivatives of formula (1) having cyclic AMP phosphodiesterase inhibitory activity have been prepared and studied for their platelet inhibition and cardiotonic properties. Thus, for example:

Meanwell, N. A., U.S. Pat. No. 4,943,573 describes a series of 2,3-dihydro-2-oxo-1H-imidazo[4,5-b]quinolin-2-ones comprising derivative of the formula (2)

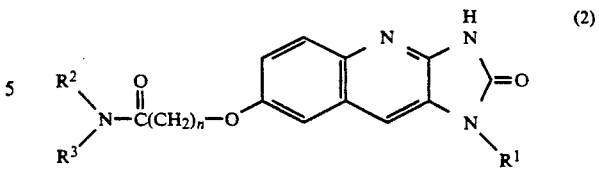

wherein n is 3 to 5; $R^1$ is hydrogen or alkyl of 1 to 4 carbon atoms; $R^2$ is hydrogen; $R^3$ is 1-piperidinylethyl, 1-benzylpiperidin-4-yl, 4-(1-piperidinyl)piperidine, (1-alkyl-2-pyrrolidinyl)alkyl where alkyl is 1 to 4 carbon atoms, 3-quinuclidinyl; $R^2$ and $R^3$ together with the nitrogen atom to which they are attached form 4-$R^4$-piperazin-1-yl wherein $R^4$ is alkyl of 1 to 7 carbon atoms, alkoxyethyl of 3 to 7 carbon atoms, pyridinyl, pyrimidinyl, tetrahydropyranylmethyl, thienylmethyl, cycloalkyl-$(CH_2)_m$ wherein m is zero or one and cycloalkyl is 5 to 7 carbon atoms except m is zero when cycloalkyl is 7 carbon atoms, benzyl, 4-fluorobenzyl, 3-trifluoromethylbenzyl, 4-alkoxybenzyl where alkoxy is 1 to 4 carbon atoms.

Among the compounds disclosed is the compound of the formula (3), identified as 1-(cyclohexylmethyl)-4-(2,3-dihydro-2-oxo-1H-imidazo[4,5-b]quinolin-7-yloxy)-1-oxybutyl]piperazine.

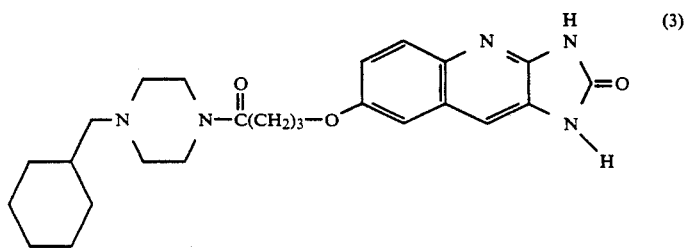

Meanwell, et al, U.S. Pat. No. 4,775,674 describe a series of 2,3-dihydro-2-oxo-1H-imidazo[4,5-b]quinolinyl ether derivatives of the formula (4)

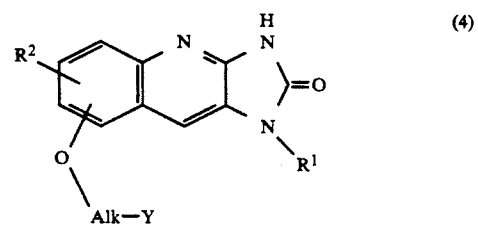

wherein $R^1$ is hydrogen, lower alkyl, benzyl; $R^2$ is hydrogen, halogen, lower alkyl, lower alkoxy; Alk is alkylene; Y is hydroxy and alkanoic or aralkanoic esters thereof, oxo ketone, dialkylamino carboxylic acid and esters, carboxamides, alkoxy, ethanolamines and cyclic carbamates thereof, tetrazoyl, and optionally substituted phenylsulfonyl.

Among the compounds disclosed is the compound of formula (5), identified in the art as 7-[4-(phenylsulfonyl)butoxy]-1,3-dihydro-2H-imidazo[4,5-b]quinolin-2-one.

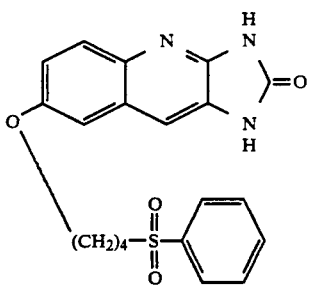

Meanwell, et al. U.S. Pat. No. 4,701,459 describe another series of 2,3-dihydro-2-oxo-1H-imidazo-[4,5-b]quinoline compounds comprising amine derivatives of formula (6)

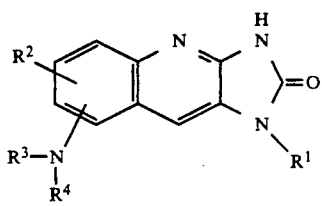

wherein $R^1$ is hydrogen, lower alkyl; $R^2$ is hydrogen, lower alkyl, lower alkoxy, halogen; $R^3$ is hydrogen, lower alkyl; $R^4$ is hydrogen, lower alkyl, alkanoyl, phenylalkanoyl wherein phenyl is optionally substituted with halogen, lower alkyl, lower alkoxy, $R^3$ and $R^4$ are joined together to form morpholinyl, piperidinyl or pyrrolidinyl optionally substituted with —$CO_2R^5$ or

wherein $R^5$ is hydrogen or lower alkyl, and $R^6$ is hydrogen, lower alkyl, cycloalkyl; 4-$R^7$-piperazinyl wherein $R^7$ is —$CO_2R^8$ wherein $R^8$ is lower alkyl, phenyl optionally substituted with up to 2 halogen, lower alkyl or lower alkoxy: phenylalkanoyl of 7 to 10 carbon wherein phenyl is unsubstituted or independently substituted with up to 2 halogen, lower alkyl, lower alkoxy.

Meanwell, et al, U.S. Pat. No. 4,668,686 describe still another series of 1,3-dihydro-2H-imidazo-[4,5-b]quninolin-2-ones comprising derivatives of formula (7)

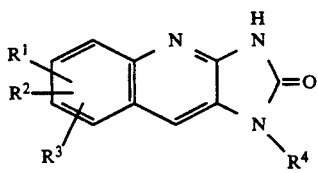

wherein $R^1$ is halogen, lower alkyl, lower alkoxy, trifluoromethyl; $R^2$ is hydrogen, halogen, lower alkyl, lower alkoxy; $R^3$ is hydrogen, halogen, lower alkyl, lower alkoxy; and $R^4$ is hydrogen or lower alkyl.

Another class of heterocyclic compounds having phosphodiesterase inhibiting and anti-platelet aggregation activity comprise the tetrahydroimidazo[2,1-b]quinazolin-2-ones of formula (8)

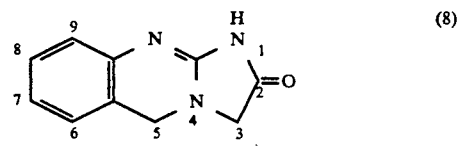

For example:

Beverung, Jr., et al, U.S. Pat. No. 3,932,407 disclose a series of compounds useful as blood platelet antiaggregative and/or antihypertensive and/or bronchodilator agents of tetrahydroimidazo[2,1-b]-quinazolin-2-one class. Anagrelide (9), a particularly preferred member of the Beverung, Jr., et al. series, has been studied extensively, e.g., J. S. Fleming, et al, New Drugs Annual: Cardiovascular Drugs, Raven Press, 277-294, N.Y. (1983).

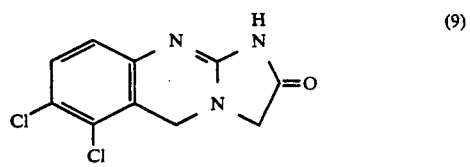

Chodnekar, et al, U.S. Pat. No. 4,256,748 describe a series of tetrahydroimidazo[2,1-b]quinazolin-2-ones of the formula (10) as inhibitors of the aggregation of blood platelets and cardiotonic activity.

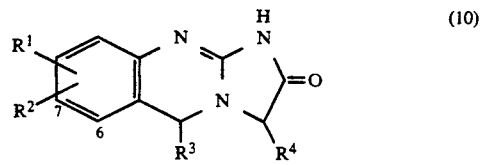

Representative of the Chodneker compounds are RO 15-2041 ($R^4$=$CH_3$, $R^3$=H, $R^2$=6—$CH_3$, $R^1$=7—Br) and RO 13-6438 ($R^4$=$CH_3$, $R^3$=H, $R^2$=6—$CH_3$, $R^1$=H).

Jones, et al, U.S. Pat. No. 4,490,371 describe another series of tetrahydroimidazo[2,1-b]quinazolin-2-one derivatives as cyclic AMP phosphodiesterase inhibitors useful as thrombogenic agents. Among the compounds disclosed is the formula (11) amide, identified in the art as lixazinone.

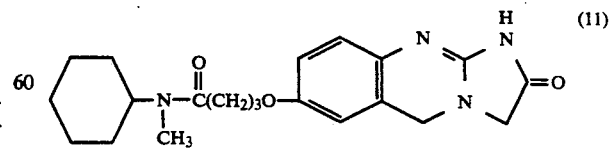

Jones, et al, European Patent Application 153152 further describe tetrahydroimidazo[2,1-b]quinazoline-ones of formula (11) as cyclic AMP phosphodiesterase inhibitors useful as antithrombogenic agents.

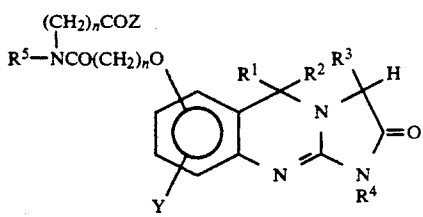

Compounds of the aforementioned patents generally display limited solubility in water, acidic or alkali media and common organic solvents.

SUMMARY OF THE INVENTION

The present invention provides novel sulfonylpiperazine derivatives of imidazo [4,5-b]quinolin-2-one which have enhanced potency and aqueous activity.

In particular, the invention relates to a series of 7-oxypropylsulfonamido-1,3-dihyrdo-2H-imidazo[4,5-b]quinolin-2-ones wherein the amide carbonyl moiety of the formula (3) compounds were replaced with a sulfonyl moiety. The sulfonamide moiety is an effective and chemically stable replacement for the labile amide functionality that contributes to low bioavailability in the formula (3) compounds. The compounds of the present invention showed enhanced water solubility compared to the formula (3) compounds.

Formula I illustrates the compounds of the invention and the ring numbering system used herein.

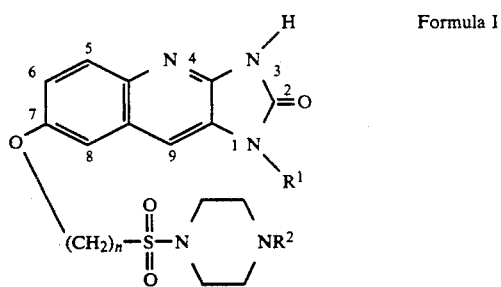

In the foregoing formula I, n, $R^1$, and $R^2$ are as described below.

The compounds of Formula I are useful as inhibitors of ADP-induced aggregation of human blood platelets in platelet rich plasma.

The compounds of Formula I have antithrombogenic and phosphodiesterase inhibition properties, and are useful in prevention or treatment of conditions involving platelet aggregation and thrombosis.

The compounds of Formula I are also considered to have antimetastatic potential in view of their platelet inhibition properties.

Another embodiment of the invention concerns pharmaceutical compositions comprised of a Formula I compound combined with at least one pharmaceutically acceptable excipient.

Yet another embodiment relates to a method for inhibiting blood platelet aggregation in a mammal which comprises administering a therapeutically effective amount of a compound of Formula 1 to a mammal in need of such treatment.

DETAIL DESCRIPTION OF THE INVENTION

The compounds of the instant invention comprise those of Formula I

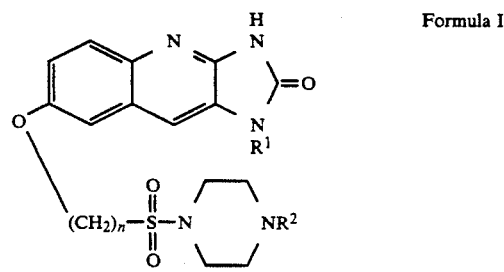

Formula I wherein $R^1$ is H, or $C_1$–$C_4$ lower alkyl;

$R^2$ is H, $(CH_2)_m R^3$; benzoxazol-2-yl, or benzothiazol-2-yl;

$R^3$ is $C_1$–$C_8$ alkyl, $C_4$–$C_8$ cycloalkyl, or substituted or unsubstituted phenyl, Wherein the substituents are halogen, alkoxy or trifluoromethyl;

m is an integer of 1–3; and n is an integer of 1–5; or pharmaceutically acceptable salt thereof.

It is understood that as used herein limitation of Formula I are defined as follows:

The term "halogen" comprehends fluorine, iodine, bromine and chlorine, and most preferably fluorine and chlorine.

The term "$C_1$–$C_8$ alkyl" refers to a branched or unbranched saturated hydrocarbon chain containing from 1 to 8 carbon atoms, for example, methyl, ethyl, n-propyl, isopropyl, butyl, isobutyl, 3-pentyl, and 4-heptyl.

The term "$C_1$–$C_4$ lower alkyl" refers to a branched or unbranched saturated hydrocarbon chain containing from 1 to 4 carbon atoms, for example, methyl, ethyl, n-propyl, isopropyl, butyl, and isobutyl.

The term "$C_4$–$C_8$ cycloalkyl" comprehends a saturated aliphatic ring containing the designated number of carbon atoms. Such radicals are, for example, cyclobutyl, cyclopentyl, cyclohexyl, cycloheptyl, and cyclooctyl.

The route to sulfonylpiperazine derivatives involves the construction of the imidazoquinolin nucleus in convergent fashion as outlined in scheme I.

Scheme I
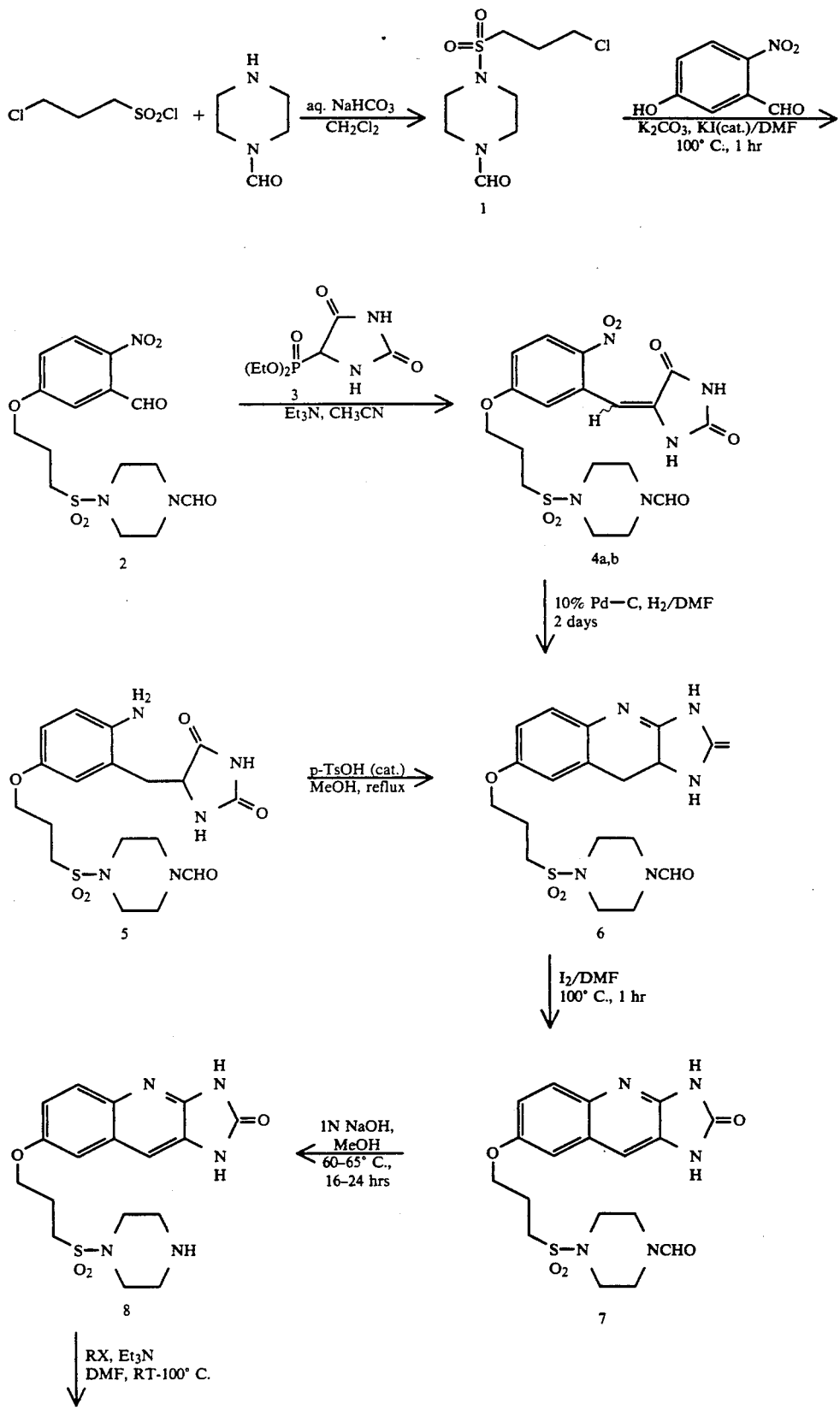

Scheme I -continued

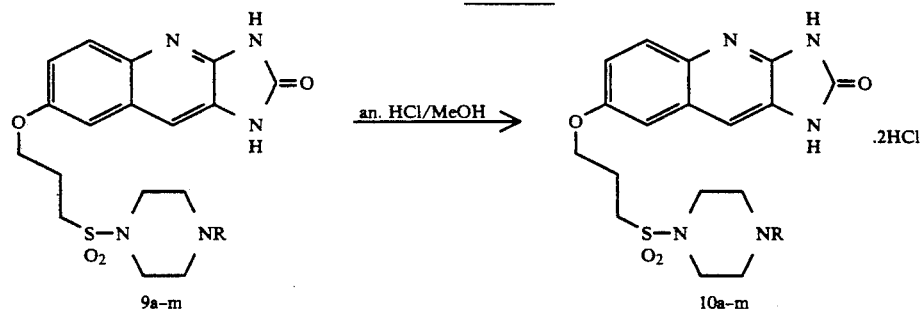

Condensation of 3-chloropropanesulfonyl chloride and 1-piperazinecarboxaldehyde gave corresponding sulfonamide 1. O-alkylation of 5-hydroxy-2-nitrobenzaldehyde with sulfonamide 1 provided the nitrobenzaldehyde derivative 2. Condensation of the anion of the phosphonate 3 (Meanwell, et al., *J. Org. Chem.*, 56: 6897–6904 (1991)) with aldehyde 2 afforded the isomeric mixture of hydantoin derivatives 4a,b. Exhaustive catalytic hydrogenation over 10% palladium on activated carbon (Pd-C) followed by cyclization and concomitant oxidation using $I_2$ in dimethylformaldehyde (DMF) provided the target imidazoquinolin, 7. Basic hydrolysis of the formamide moiety of 7 furnished the N-H congener 8 which was N-alkylated with variety of alkylating agents. Alkylation of sulfonylpiperazine moiety of 8 found to be quite general when triethylamine was used as the acid scavenger. Finally the target imidazoquinolines were converted to their hydrochloride salts by reacting with anhydrous hydrogen chloride (HCl) in methanol.

In Vitro Inhibition of Human Platelet Aggregation

The aggregometer method of Born, G. V. R., *J. Physiol.*, (London), 162, 67–68, (1962) as modified by Mustard, J. F., et al., *J. Lab. Clin. Med.*, 64, 548–599, (1964) was used to assess the in vitro activity of the various compounds as to the inhibition of adenosine diphosphate (ADP) and collagen-induced platelet aggregation. The human volunteer donor's arm is cleansed with 70% ethyl alcohol. A sterile 20 ml syringe and needle are used to withdraw 20 ml of blood. The blood is immediately added to a test tube containing 3.8% sodium citrate to prevent clotting (1 part citrate to 9 parts blood).

Platelet rich plasma (PRP) was separated by centrifugation for 10 minutes at 1000 rpm (140xg) from citrated (3.8%) human blood. All glassware used for preparation of PRP is silicon treated. ADP in final concentration of 0.5 μg/mL or 0.05 mL of a collagen suspension prepared according to the method described by Evans, G., et al., *J. Exp. Med.*, 128, 877–894, (1968) was used to induce aggregation. The various compounds tested were dissolved in dimethylsulfoxide (DMSO) so that 5 μl added to the platelet rich plasma would yield the desired test concentration. Vehicle control trials were done and compared with aggregation induced in platelet rich plasma containing various concentrations of the test compounds. Dose response curves were obtained and Inhibitor Concentration ($IC_{50}$) values calculated. In this test, the $IC_{50}$ values for dipyridamole, a clinically useful antithrombogenic agent, are 512 μg/ml vs. ADP and 245 μg/ml vs collagen. Results for 50% inhibition of ADP-induced aggregation are given hereinafter.

The target compounds were evaluated as inhibitors of ADP-induced aggregation of human blood platelets in platelet-rich-plasma (PRP) in vitro. The test compounds were incubated at about 37° C. in PRP for about 3 minutes prior to the addition of sufficient ADP to provide a final ADP concentration of 5.86 mM.

TABLE I

Inhibition of ADP-induced Human Platelet Aggregation by Test Compounds

| Cmpd # | $IC_{50}$ vs ADP in human PRP, μg/mL | Aqueous Solubility mg/mL |
|---|---|---|
| 7 | 5.6 | <1* |
| 8 | 7.2 | ~1* |
| 10a | 6.4 | >20 |
| 9c | 0.059 | ~1* |
| 10c | 0.039 | >20 |
| 10d | 0.16 | >20 |
| 10e | 0.32 | >20 |
| 10f | 0.27 | >20 |
| 10g | 0.064 | >20 |
| 10h | 1.4 | >20 |
| 10i | 2.8 | ~1 |
| 10j | 1.2 | <5 |
| 10k | 0.6 | <10 |
| 10l | 0.09 | >10 |
| 10m | 0.2 | ~2 |

*Aqueous Solubility of Free Base

The Formula I compounds or pharmaceutically acceptable salts thereof have pharmacological properties which make them useful as inhibitors of ADP-induced aggregation of human blood platelets in platelet rich plasma.

Another embodiment of the invention concerns pharmaceutical compositions comprised of a Formula I compound combined with at least one pharmaceutically acceptable excipient.

Yet another embodiment relates to a method for inhibiting blood platelet aggregation in a mammal which comprises administering a therapeutically effective amount of a compound of Formula I to a mammal in need of such treatment.

The dosage employed in the instant therapeutic methods will vary with the form of administration, the particular compound chosen, the subject being tested and the effect desired. Suitable effective doses in animals range from 0.01 to 50 mg/Kg body weight orally and from 0.001 to 20 mg/kg body weight parenterally (generally characterized as subcutaneous, intramuscular, and intravenous injection). It is contemplated that the effective unit dose in man will range from 0.1 to 50 mg/Kg and preferably from 0.5 to 30 mg/Kg administered one to three times a day. In accordance with conventional clinical practice, the effective dose can be determined by administering a Formula I compound at a dosage substantially less than the does of the compound which is thought to be effective and then increasing the dosage in small increments until the desired effect is achieved.

In carrying out the instant therapeutic methods, the active ingredient of Formula I and pharmaceutically acceptable acid addition salts thereof are preferably administered with a pharmaceutically acceptable carrier and such compositions constitute part of the instant invention. Suitable dosage forms for oral use are tablets, dispersible powders, granules, capsules, syrups and elixirs. Examples of parenteral forms are solutions, suspensions, dispersions, emulsions, and the like. The compositions for oral use may contain one or more conventional adjuvants, such as sweetening agents, flavoring agents, coloring agents and preserving agents, in order to provide a composition of suitable pharmaceutical elegance. Tablets may contain the active ingredient in admixture with conventional pharmaceutical acceptable excipients including inert diluents such as calcium carbonate, sodium carbonate, lactose and talc; granulating and disintegrating agents such as starch and alginic acid; binding agents such as starch, gelatin and acacia and lubricating agents such as magnesium stearate, stearic acid and talc. The tablets may be uncoated by known techniques to delay disintegration and absorption in the gastrointestinal tract and thereby provide a sustained action over a longer period. Similarly, suspension, syrups and elixirs may contain the active ingredient in admixture with any of the conventional excipients utilized for the preparation of such compositions such as suspending agents (e.g., methylcellulose, tragacanth, and sodium alginate), wetting agents (e.g., lecithin, polyoxyethylene stearate) and preservatives such as ethyl-p-hydroxybenzoate. Capsules may contain the active ingredient alone or admixed with an inert solid diluent such as calcium carbonate, calcium phosphate and kaolin. The injectable compositions are formulated as known in the art and may contain appropriate dispersing or wetting agents and suspending agents identical or similar to those mentioned above.

All publications cited in this specification are indicative of the level of skill of those skilled in the art to which this invention pertains. Each publication is individually incorporated herein by reference in the location where it is cited.

The compounds which constitute the invention and their methods of preparation will appear more fully from a consideration of the following examples. The compounds which are not shown by specific example are readily prepared by analogous procedure. The following examples are given by way of illustration and are not to be construed as limiting the invention in any way inasmuch as many variations of the invention are possible within the spirit of the invention.

All temperatures are degrees Centigrade and melting points taken with a Thomas Hoover capillary apparatus are uncorrected. Conventional abbreviations are employed in reporting Nuclear Magnetic Resonance (NMR) spectral data with tetramethylsilane as internal reference and chemical shift data values in parts per million.

EXAMPLE 1

4-(3-Chloropropanesulfonyl)piperazine-1-carboxaldehyde (1)

A solution of 1-piperazinecarboxaldehyde (21.5 g, 0.19 mol) in dichloromethane ($CH_2Cl_2$) (50 mL) was added dropwise over about 20 minutes to a stirred bi-phase mixture of 3-chloropropanesulfonyl chloride (27.7 g, 0.16 mol) in $CH_2Cl_2$ (150 mL) and saturated $NaHCO_3$ solution (20 g in 200 mL of water) at room temperature. Resultant mixture was stirred at room temperature for about 4 hours. Layers were separated and the aqueous layer was re-extracted with $CH_2Cl_2$ (2×150 mL). Combined $CH_2Cl_2$ extracts were washed consecutively with 1N HCl (100 mL), 10% sodium carbonate ($Na_2CO_3$) solution, water, brine and then dried magnesium sulfate ($MgSO_4$). Filtration followed by rotary evaporation of $CH_2Cl_2$ gave 33.7 g (84.5%) of white solid which was recrystallized from ethyl acetate/hexanes to afford 30.5 g (76.4%) of pure 1 : mp 84°-85° C.; IR (KBr, $cm^{-1}$) 1680, 1340, 1155; $^1$H NMR (300 MHz, $CDCl_3$) δ2.24 (2H, m), 3.05 (2H, t, J=7.5 Hz), 3.24 (2H, t, J=5.2 Hz), 3.29 (2H, m), 3.44 (2H, t, J=5.0 Hz), 3.62 (4H, m), 8.02 (1H, s); $^{13}$C NMR (75 MHz, $CDCl_3$) δ26.42, 40.07, 43.03, 45.41, 45.69, 46.41, 47.07, 161.03; MS m/e 255 (MH+).

Anal. Calcd. for $C_8H_{15}ClN_2O_3S$:
C, 37.72; H, 5.94; N, 10.99.
Found: C, 37.83; H, 5.83; N, 10.98.

EXAMPLE 2

4-[3-(3-Formyl-4-nitrophenoxy)propyl]sulfonyl]-1-piperazine carboxaldehyde (2)

A stirred suspension of 5-hydroxy-2-nitrobenzaldehyde (17.1g, 0.102 mol), 4-(3-chloropropanesulfonyl)-piperazine-1-carboxaldehyde (26.0 g, 0.102 mol), pulverized anhydrous $K_2CO_3$ (17 g, 0.12 mol) and KI (3.4 g, 0.02 mol) in anhydrous DMF (100 mL) was heated at about 100°-105° C. under nitrogen for about 1.25 hours. Reaction mixture was allowed to cool and then DMF was rotary evaporated at about 50° C. bath temperature. Resultant thick slurry was suspended in $CH_2Cl_2$ (400 mL) and then water was added with stirring. Layers were separated and the aqueous layer was re-extracted with $CH_2Cl_2$ (2×200 mL). Combined $CH_2Cl_2$ extracts were washed consecutively with 10% $Na_2CO_2$ solution (2×200 mL), water, brine and then dried ($MgSO_4$). Filtration followed by rotary evaporation of $CH_2Cl_2$ gave light-yellow semi-solid which was triturated with $CH_2Cl_2$-ether to afford 36.7 g (93.4%) of pure 2: mp 108°-110° C.; IR (KBr, $cm^{-1}$), 1678, 1502, 1340, 1328, 1236, 1146, 825; $^1$H NMR (300 MHz, DMSO-$d_6$) δ2.15 (2H, m), 3.16 (2H, t, J=5.1 Hz), 3.25 (4H, m), 3.44 (4H, m), 4.26 (2H, t, J=6.1 Hz), 7.25 (1H, d, J=2.8 Hz), 7.36 (1H, dd, J=9.0 and 2.8 Hz), 8.04 (1H, s), 8.18 (1H, d, J=9.0 Hz), 10.27 (1H, s); $^{13}$C NMR (75 MHz, DMSO-$d_6$) δ22.66, 44.68, 44.80, 45.05, 45.82, 67.01, 114.21, 118.52, 127.36, 134.25, 141.97, 161.15, 162.59, 189.94; MS m/e 386 (MH+).

Anal. Calcd. for $C_{15}H_{19}N_3O_7S$:
C, 46.75; H, 4.97; N, 10.90.
Found: C, 47.04; H, 4.90; N, 11.01.

EXAMPLE 3

(E,Z)4-[[3-[3-[(2,5-Dioxo-4-imidazolidinylidene)methyl]-4-nitrophenoxy]propyl]sulfonyl]-1-piperazinecarboxaldehyde (4a,b)

To a stirred suspension of diethyl 2,5-dioxo-4-imidazolidinylphosphonate (25.7 g, 0.11 mol) in acetonitrile (100 mL), triethylamine (20 mL, 0.14 mol) was added under nitrogen. To the resultant pale-yellow solution of the phosphonate anion, a solution of the aldehyde 2 (35 g, 0.91 mol) was added dropwise over about 30 minutes. The resultant deep-red solution was stirred at room temperature for about 4.5 hours. Acetonitrile and excess isoamylamine (Et3N) was rotary evaporated at 40°-50° C. bath temperature. Resultant viscous oil was treated with 0.05N HCl (200 mL) with vigorous agitation. Finely divided solid was filtered off and washed with water and then air dried overnight. Air dried solid was finely ground and then dried in vacuo to give 41.8 g (98.5%) of pure isomeric mixture of 3: IR (KBr, cm$^{-1}$) 1770, 1730, 1654, 1510, 1370, 1338, 1260, 1144, 835; MS m/e 468 (MH$^{30}$).

Anal. Calcd. for $C_{18}H_{21}N_5O_8S$:
C, 46.25; H, 4.52; N, 14.98.
Found: C, 46.28; H, 4.34; N, 14.49.

EXAMPLE 4

4-[[3-[4-Amino-3-(2,5-dioxo-4-imidazolidinyl)methyl]-phenoxy]propyl]sulfonyl]-1-piperazinecarboxaldehyde (5)

Hydrogenation of 4a,b was carried out in two equal batches. A suspension resulted from addition 10% Pd-C (2.0 g) to a solution of 4a,b (2×20.5 g, 0.088 mol) in DMF (400 mL) was hydrogenated at 60-70 psi in a Parr apparatus for about 19 hours. Additional fresh 10% Pd-C (2 g) was added and continued to hydrogenate for an additional 24 hours. Reduction was monitored by thin layer chromatography (TLC) and NMR. The suspension was filtered through celite and the celite filtercake was thoroughly washed with DMF. Combined filtrate and washings were rotary evaporated under reduced pressure at about 50° C. bath temperature to give 38.5 g of crude product. An analytically pure sample was prepared by triturating with methanol. mp 200°-203° C. (dec.); IR (KBr, cm$^{-1}$) 3500-2700, 1766, 1724, 1640, 1326, 1260, 1144, 815; $^1$H NMR (300 MHz, DMSO-d$_6$) δ2.03 (2H, m), 2.71 (1H, dd, J=12.9 and 5.2 Hz), 2.85 (1H, dd, J=12.9 and 5.2 Hz), 3.16 (4H, m), 3.20 (2H, t, J=6.0 Hz), 3.33 (1H, s), 3.43 (4H, m), 3.89 (2H, t, J=6.1 Hz), 4.32 (1H, t, J=5.2 Hz), 4.42 (1H, s), 6.57 (3H, s), 7.76 (1H, s), 8.02 (1H, s), 10.55 (1H, s). $^{13}$C NMR (75 MHz, DMSO-d$_6$) δ23.03, 32.21, 44.70, 44.80, 45.35, 45.81, 57.35, 65.93, 113.98, 116.35, 117.54, 121.44, 140.63, 149.78, 157.24, 161.15, 176.08; MS m/e 440 (MH+).

Anal. Calcd. for $C_{18}H_{25}N_5O_6S$:
C, 49.19; H, 5.73; N, 15.93.
Found: C, 49.30; H, 5.74; N, 15.67.

EXAMPLE 5

4-[[3-(2,3,9,9a-Tetrahydro-2-oxo-1H-imidazo[4,5-b]quinolin-7-yloxy)propyl]sulfonyl]-1-piperazinecarboxaldehyde (6)

A stirred suspension of crude 5 (38 g) and p-toluenesulfonic acid (1 g) in anhydrous methanol (500 mL) was heated to reflux under nitrogen for about 6 hours. The suspension was allowed to cool to room temperature and filtered, washed with methanol and then air dried. Finally solid was dried in vacuo to provide 35.4 g of pure 6: mp 285°-288° C.; IR (KBr, cm$^{-1}$) 3600-3100, 1674, 1644, 1340, 1278, 1148; $^1$H NMR (300 MHz, DMSO-d$_6$) δ2.07 (2H, m), 2.61 (1H, t, J=14.9 Hz), 2.95 (1H, dd, J=14.9 and 7.2 Hz), 3.19 (6H, m), 3.43 (4H, m), 4.00 (2H, t, J=6.0 Hz), 4.19 (1H, dd, J=14.9 and 9.0 Hz), 6.77 (1H, dd, J=8.6 and 2.5 Hz), 6.83 (1H, d, J=2.5 Hz), 6.91 (1H, d, J=8.5 Hz), 7.65 (1H, s), 8.03 (1H, s), 10.57 (1H, s); $^{13}$C NMR (75 MHz, DMSO-d$_6$) δ22.91, 31.49, 44.74, 45.21, 45.81, 50.77, 65.75, 113.61, 115.29, 121.95, 124.65, 135.78, 154.35, 161.15, 163.88, 166.96; MS m/e 422 (MH+).

Anal. calcd. for $C_{18}H_{23}N_5O_5S$:
C, 51.29; H, 5.50; N, 16.62.
Found: C, 51.28; H, 5.49; N, 16.43.

EXAMPLE 6

3-[[(2,3-Dihydro-2-oxo-1H-imidazo[4,5-b]quinolin-7-yl)oxy]propyl]sulfonyl]-1-piperazinecarboxaldehyde (7)

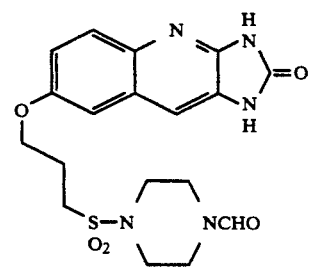

To a stirred partial solution of 6 (32.8 g, 0.078 mol) in anhydrous DMF (950 mL) heated to about 100°-110° C., iodine (20.7 g, 0.082 mol) was added in small portions under nitrogen. Resultant brown solution was maintained at about 100°-110° C. for about 1 hour. Reaction mixture was allowed to cool to about 50°-60° C. and then DMF was rotary evaporated under reduced pressure at about 50° C. bath temperature. Resultant viscous residue was neutralized with saturated sodium bicarbonate (NaHCO$_3$) (100 mL) and then treated with 10% sodium thiosulfate (Na$_2$S$_2$O$_3$) solution (300-400 mL). Resultant suspension was stirred until iodine color disappears and then filtered, washed with water, air dried overnight. Finally slightly wet solid was triturated with boiling methanol to provide 32.1 g (98.3%) of pure 7: mp 315°-318° C.; IR (KBr, cm$^{-1}$) 3600-2200, 1706, 1670, 1320, 1234, 1146; $^1$H NMR (300 MHz, DMSO-d$_6$) δ2.15 (2H, m), 3.22 (6H, m), 3.43 (4H, m), 4.13 (2H, t, J=5.9 Hz), 7.14 (1H, dd, J=9.1 and 2.4 Hz), 7.30 (1H, d, J=2.4 Hz), 7.49 (1H, s), 7.66 (1H, d, J=9.1 Hz), 8.02 (1H, s), 10.95 (1H, s), 11.36 (1H, s); $^{13}$C NMR (75 MHz, DMSO-d$_6$) δ22.93, 44.68, 44.81, 45.29, 45.82, 65.73, 107.42, 109.45, 118.00, 125.09, 126.43, 128.17, 138.17, 145.47, 154.43, 155.43, 161.14; MS m/e 420 (MH+).

Anal Calcd. for $C_{18}H_{21}N_5O_5S$: 0.53 H$_2$O:
C, 50.46,; H, 50.17; N, 16.34.
Found: C, 50.47; H, 5.04; N, 16.27.

EXAMPLE 7

1-[[3-[(2,3-Dihydro-2-oxo-1H-imidazo[4,5-b]quinolin-7-yl)oxy]propyl]sulfonyl]piperazine (8)

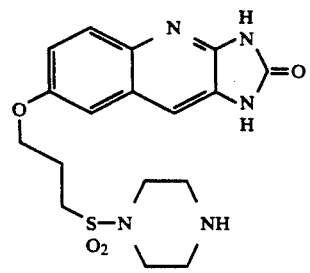

A stirred partial solution of (30 g, 0.0715 mol) in methanol (400 mL) and 1N NaOH solution (160 mL) was heated to reflux for about 23 hours. At reflux suspension clears up to form a brown solution. The reaction mixture was allowed to cool to about 40°-50° C. and then methanol was rotary evaporated. Aqueous residue was transferred to a beaker and cooled in an ice bath and then acidified with 3N HCl (50-60 mL). Finally pH of the suspension was adjusted with sald. NaHCO₃ to 7-8. Precipitate was filtered off and washed with water and then air dried. Slightly wet product was triturated with boiling methanol to provide 26.9 g 96%) of pure 8: mp 293°-295° C.; IR (KBr, cm⁻¹) 3600-2300, 1718, 1358, 1154, 1250, 830; ¹H NMR (300 MHz, DMSO-d₆) δ2.15 (2H, m), 2.71 (4H, m), 3.07 (4H, m), 3.19 (2H, t, J=6.2 Hz), 3.31 (1H, s), 4.14 (2H, t, J=6.0 Hz), 7.16 (1H, dd, J=9.1 and 2.7 Hz), 7.31 (1H, d, J=2.7 Hz), 7.50 (1H, s), 7.67 (1H, d, J=9.1 Hz), 10.95 (1H, s), 11.28 (1H, s); ¹³C NMR (75 MHz, DMSO-d₆) δ22.95, 44.31, 45.21, 46.17, 65.77, 107.41, 109.46, 118.01, 125.10, 126.45, 128.19, 138.17, 145.47, 154.46, 155.43; MS m/e 392.

Anal Calcd. for $C_{17}H_{21}N_5O_4S \cdot 0.49 H_2O$:
C, 51.10; H, 5.48; N, 17.66.
Found: C, 51.51; H, 5.30; N, 17.37.

General Procedure for the N-alkylation of Compound (8)

In general alkylation was done in anhydrous DMF in the presence of Et₃N as the acid quencher. Reaction temperature and time was varied upon the nature of alkylating agent. In a typical procedure a stirred suspension of compound (8) (1 mmol), Et₃N (2-4 mmol) and alkylating agent (2-4 mmol) in anhydrous DMF was maintained at room temperature or heated to 60°-100° C. depending on the alkylating agent. Progress of the reaction was monitored by TLC. The reaction mixture was allowed to cool to room temperature and then poured into water. pH of the resultant suspension was adjusted to 7-8 with saturated NaHCO₃ solution. Precipitated product was filtered off, washed with water and then air dried overnight. Crude product was triturated with boiling methanol and then converted to dihydrochloride salt by reacting with saturated solution of anhydrous HCl gas in anhydrous methanol either at room temperature or reflux. Upon cooling dihydrochloride salt was precipitated out from the solution or precipitated out by addition of anhydrous ether. Finally dihydrochloride salts were dried in a drying pistol at about 100°-110° C. in vacuo.

EXAMPLE 8

1-[[3-[(2,3-Dihydro-2-oxo-1H-imidazo[4-5-b]quinolin-7-yl)oxy]propyl]sulfonyl]piperazine dihydrochloride (10a)

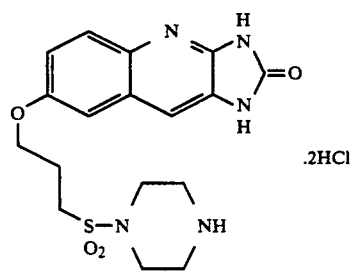

mp 237°-240° C.; IR (KBr, cm⁻¹) 3600-2300, 1758, 1328, 1232, 1148, 830; ¹H NMR (300 MHz, DMSO-d₆) δ2.16 (2H, m), 3.14 (4H, m), 3.34 (2H, t, J=7.6 Hz), 3.48 (4H, m), 4.16 (2H, t, J=6.0 Hz), 7.22 (1H, dd, J=9.1 and 2.7 Hz), 7.40 (1H, d, J=2.7 Hz), 7.64 (1H, s), 7.77 (1H, d, J=9.1 Hz), 9.2 (1H, brd s), 9.69 (2H, s), 11.29 (1H s); ¹³C NMR (75 MHz, DMSO-d₆) δ22.95, 42.10, 42.56, 45.80, 65.80, 107.77, 110.98, 188.63, 125.64, 126.20, 126.36, 135.52, 144.73, 154.81, 155.06; MS m/e 392 (MH+).

Anal. Calcd. for $C_{17}H_{21}N_5O_4S \cdot 2HCl$:
C, 43.97; H, 4.99; N, 15.08.
Found: C, 44.21; N, 5.04; N, 14.52.

EXAMPLE 9

3-[[(2,3-Dihydro-2-oxo-1H-imidazo[4,5-b]quinolin-7-yl)oxy]propyl]sulfonyl]-4-(2-phenylethyl)piperazine dihydrochloride (10k)

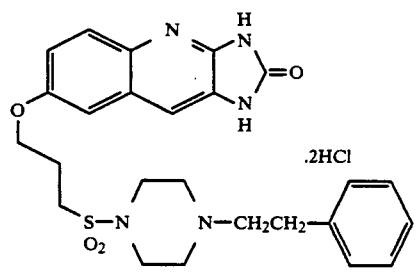

EXAMPLE 10

1-[[3-[(2,3-Dihydro-2-oxo-1H-imidazo[4,5-b]quinolin-7-yl)oxy]propyl]sulfonyl]-4-(phenylmethyl)piperazine dihydrochloride (10c)

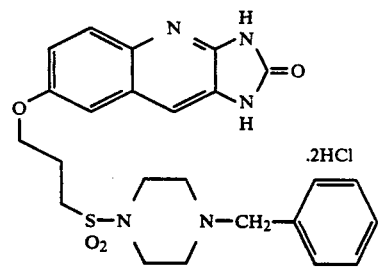

mp 261°-264° C. IR (KBr, cm⁻¹) 3600-2200, 1750, 1638, 1346, 1232, 1148, 700, 756; ¹H NMR (300 MHz, DMSO-d₆) δ2.15 (2H, m), 3.08 (2H, m), 3.33 (4H, m), 3.44 (2H, t, J=11.8 Hz), 3.74 (2H, m), 4.15 (2H, t, J=6 Hz), 4.33 (2H, s), 7.20 (1H, d, J=9.1 Hz), 7.42 (4H, m), 7.61 (3H, m), 7.74 (1H, d, J=9.1 Hz), 7.5 (2H, brd s), 11.21 (1H, s), 11.88 (1H, brd s); ¹³C NMR, DMSO-d₆) d 22.95, 42.03, 45.96, 50.21, 58.38, 65.72, 107.66, 110.60, 118.47, 125.50, 126.25, 126.82, 128.80, 129.46, 129.52, 131.49, 136.18, 144.92, 154.69, 155.15; MS m/e 482 (MH+).

Anal. Calcd. for $C_{24}H_{27}N_5S \cdot 2HCl \cdot 0.36 H_2O$:
C, 51.38; H, 5.34; N, 12.48.
Found: C, 51.38; H, 5.34; N, 12.23.

EXAMPLE 11

1-[[3-[(2,3-Dihydro-2-oxo-1H-imidazo[4,5-b]quinolin-7-yl)oxy]propyl]sulfonyl]-4-(4-fluorophenylmethyl)piperazine dihydrochloride (10d)

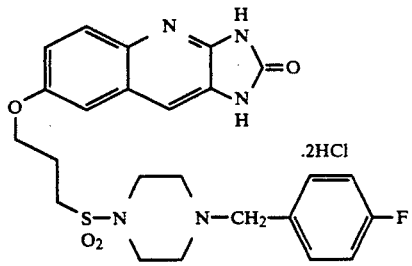

mp 282°–285° C.; IR (KBr, cm$^{-1}$) 3600–2400, 1742, 1328, 1232, 1152; $^1$H NMR (300 MHz, DMSO-d$_6$) δ2.15 (2H, m), 3.08 (2H, m), 3.34 (4H, m), 3.43 (2H, t, J=12.0 Hz), 3.75 (2H, m), 4.15 (2H, t, J=6.0 Hz), 4.34 (2H, s), 6.67 (2H, brd s), 7.20 (1H, dd, J=9.3 and 2.7 Hz), 7.28 (2H, t, J=8.8 Hz), 7.38 (1H, d, J=2.7 Hz), 7.60 (1H, s), 7.71 (3H, m), 11.20 (1H, s), 11.94 (1H, brd s); $^{13}$C NMR (75 MHZ, DMSO-d$_6$) δ22.96, 42.06, 45.98, 50.12, 57.45, 65.72, 107.64, 110.54, 115.58, 115.86, 118.45, 125.47, 125.80, 126.27, 126.89, 133.90, 136.30, 144.96, 154.68, 155.17; MS m/e 500 (MH+).

Anal. Calcd. for C$_{24}$H$_{26}$FN$_5$O$_4$S. 2HCl:
C, 50.35; H, 4.93; N, 12.23.
Found: C, 50.26; H, 5.14; N, 11.80.

EXAMPLE 12

1-[[3-[(2,3-Dihydro-2-oxo-1H-imidazo[4,5-b]quinolin-7-yl)oxy]propyl]sulfonyl]-4-(4-chlorophenylmethyl)piperazine dihydrochloride (10e)

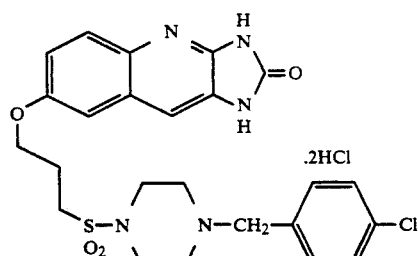

mp 272°–275° C.; IR (KBr, cm$^{-1}$) 3600–2300, 1762, 1330, 1232, 1150, 825; $^1$H NMR (300 MHz, DMSO-d$_6$) δ2.15 (2H, m), 3.07 (2H, m), 3.32 (4H, m), 3.43 (2H, t, J=10.9 Hz), 3.72 (2H, m), 4.15 (2H, t, J=5.4 Hz), 4.34 (2H, s), 5.7 (2H, brd s), 7.19 (1H, dd, J=9.0 and 7.37 (1H, s), 7.51 (2H, d, J=8.3 Hz), 7.59 (1H, s), 7.66 (2H, d, J=8.3 Hz), 7.72 (1H, d, J=9.0 Hz), 11.18 (1H, s), 11.96 (1H, brd s); $^{13}$C NMR (75 MHZ, DMSO-d$_6$) δ22.96, 42.05, 45.99, 50.21, 57.45, 65.71, 65.71, 107.62, 110.43, 118.40, 125.43, 126.28, 127.02, 128.45, 128.82, 133.44, 134.45, 136.48, 145.00, 154.65, 155.19; MS m/e 516 (MH+).

Anal. Calcd. for C$_{24}$H$_{26}$ClN$_5$O$_4$S. 2HCl. 0.59H$_2$O:
C, 48.08; H, 4.91; N, 11.68.
Found: C, 48.08; H, 5.00; N, 11.33.

EXAMPLE 13

1-[[3-[(2,3-Dihydro-2-oxo-1H-imidazo[4,5-b]quinolin-7-yl)oxy]propyl]sulfonyl]-4-(cyclohexylmethyl)piperazine dihydrochloride (10g)

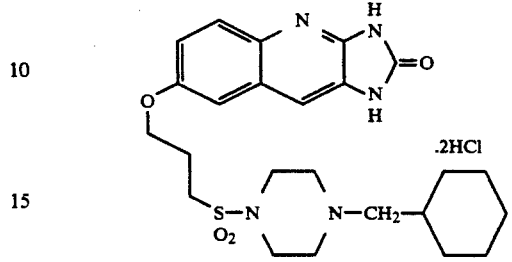

mp 296°–298° C.; IR (KBr, cm$^{-1}$) 3600–2200, 1750, 1320, 1230, 1140, 840; $^1$H NMR (300 MHz, DMSO-d$_6$) δ0.91 (2H, m), 1.18(3H, m), 1.61 (3H, m), 1.79 (3H, m), 2.17 (2H, m), 2.90 (2H, t, J=5.5 Hz), 3.03 (2H, m), 3.35 (2H, m), 3.57 (4H, m), 3.68 (2H, m), 4.16 (2H, t, J=6.0 Hz), 5.66 (2H, brd s), 7.21 (1H, dd, J=9.1 and 2.7 Hz), 7.40 (1H, d, J=2.7 Hz), 7.62 (1H, s), 7.75 (1H, d, J=9.1 Hz), 11.03 (1H, brd s), 11.25 (1H, s); $^{13}$C NMR (75 MHZ, DMSO-d$_6$) δ24.66, 26.71, 27.17, 32.38, 33.64, 43.51, 47.58, 52.78, 63.17, 67.44, 109.43, 112.47, 120.25, 127.28, 127.94, 128.31, 137.58, 146.54, 156.44, 156.80; MS m/e 488 (MH+).

Anal. Calcd. for C$_{24}$H$_{33}$N$_5$O$_4$S. 2HCl. 0.7 H$_2$O:
C, 50.29; H, 6.40; N, 12.22.
Found: C, 50.28; H, 6.38; N, 12.41.

EXAMPLE 14

1-[[3-[(2,3-Dihydro-2-oxo-1H-imidazo[4,5-b]quinolin-7-yl)oxy]propyl]sulfonyl]-4-(2-cyclohexylethyl)piperazine dihydrochloride (10j)

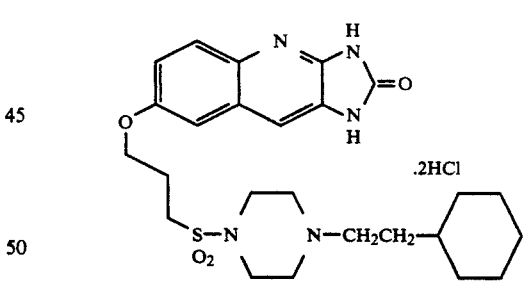

mp 295°–298° C.; IR (KBr, cm$^{-1}$) 3600–2200, 2930, 1760, 1324, 1232, 1142, 832; $^1$H NMR (300 MHz, DMSO-d$_6$) δ0.86 (2H, m), 1.09 (4H, m), 1.61 (6H, m), 2.17 (2H, m), 3.01 (3H, m), 3.38 (8H, m), 3.71 (2H, m), 4.14 (2H, t, J=6.0 Hz), 7.2 (2H, very brd s), 7.19 (1H, dd, J=9.1 and 2.7 Hz), 7.37 (1H, d, J=2.7 Hz), 7.57 (1H), s), 7.72 (1H, dd, J=9.1 Hz), 11.13 (1H, s), 11.43 (1H, brd s); $^{13}$C NMR (75 MHz, DMSO-d$_6$) δ22.97, 25.51, 25.90, 30.06, 32.40, 34.95, 42.14, 45.91, 50.43, 53.66, 65.68, 107.61, 110.18, 118.30, 125.37, 126.33, 127.33, 136.93, 145.14, 154.60, 155.25; MS m/e 502 (MH+).

Anal. Calcd. for C$_{25}$H$_{35}$N$_5$O$_4$S. 2HCl. 0.81 H$_2$O:
C, 50.97; H, 6.61; N, 11.89.
Found: C, 50.97; H, 6.25; N, 12.23.

EXAMPLE 15

1-[[3-[(2,3-Dihydro-2-oxo-1H-imidazo[4,5-b]quinolin-7-yl)oxy]propyl]sulfonyl]-4-[(3-trifluoromethylphenyl)-methyl]piperazine dihydrochloride (10m)

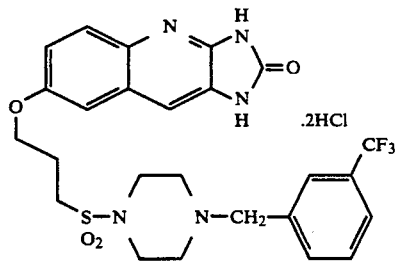

mp 260°-262° C.; IR (KBr, cm$^{-1}$) 3700-2100, 1742, 1330, 1236, 1150, 1132, 816, 752; $^1$H NMR (300 MHz, DMSO-d$_6$) δ2.16 (2H, m), 3.12 (2H, m), 3.34 (4H, m), 3.44 (2H, t, J=11.5 Hz), 3.74 (2H, m), 4.15 (2H, t, J=6.0 Hz), 4.47 (2H, s), 6.62 (2H, brd s), 7.20 (1H, dd, J=9.1 and 2.7 Hz), 7.37 (1H, d, J=2.7 Hz), 7.60 (1H, s), 7.66 (1H, d, J=7.7 Hz), 7.71 (1H, t, J=7.7 Hz), 7.80 (1H, d, J=7.7 Hz), 7.96 (1H, d, J=9.1 Hz), 8.08 (1H, s); $^{13}$C NMR (75 MHZ, DMSO-d$_6$) δ22.96, 42.06, 46.01, 50.35, 57.55, 65.72, 107.64, 110.61, 118.47, 125.49, 125.77, 126.25, 126.79, 128.28, 129.20, 129.62, 129.89, 130.82, 135.73, 136.15, 144.90, 154.70, 155.14; MS m/e 550 (MH+).

Anal. Calcd. for C$_{25}$H$_{26}$N$_5$O$_4$S. 2HCl:
C, 48.23; H, 4.53; N, 11.25.
Found: C, 48.43; H, 4.60; N, 11.22.

EXAMPLE 16

1-(Benzoxazol-2-yl)-4-[[3-[(2,3-dihydro-2-oxo-1H-imidazo[4,5-b]quinolin-7-yl)oxy]propyl]sulfonyl]piperazine dihydrochloride (10h)

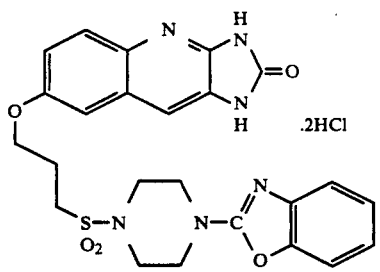

mp 348°-350° C. (dec); IR (KBr, cm$^{-1}$) 3600-2300, 1764, 1684, 1324 1240, 1142; $^1$H NMR (300 MHz, DMSO-d$_6$) δ2.17 (2H, m), 3.29 (2H, t, J=7.4 Hz), 3.38 (4H, m), 3.73 (4H, m), 4.15 (2H, t, J=6.0 Hz), 7.08 (1H, t, J=7.8 Hz), 7.20 (2H, m), 7.32 (1H, d, J=7.7 Hz), 7.39 (1H, d, J=2.4 Hz), 7.45 (1H, d, J=7.9 Hz), 7.65 (1H, s), 7.77 (1H, d, J=9.1 Hz); $^{13}$C NMR (75 MHz, DMSO-d$_6$) δ22.89, 44.34, 45.30, 45.43, 65.84, 107.74, 109.42, 111.22, 115.32, 118.73, 121.48, 124.50, 125.70, 125.98, 126.12, 134.97, 140.31, 144.55, 147.70, 154.86 154.98, 160.58; MS m/e 509 (MH+).

Anal. Calcd. for C$_{24}$H$_{24}$N$_6$O$_5$S. 2HCl:
C, 49.57; H, 4.50; N, 14.45.
Found: C, 49.93; H, 4.57; N, 14.37.

EXAMPLE 17

1-[[3-[(2,3-Dihydro-2-oxo-1H-imidazo[4,5-b]quinolin-7-yl)oxy]propyl]sulfonyl]-4-[(4-methoxyphenylmethyl)piperazine dihydrochloride (10f)

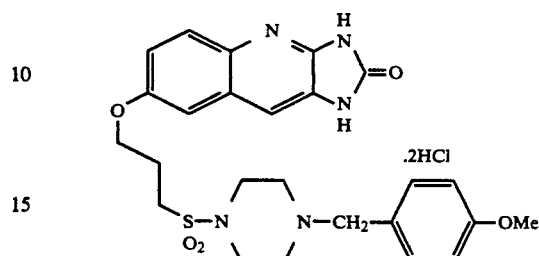

mp 210°-213° C.; IR (KBr, cm$^{-1}$) 3600-2300, 1728, 1336, 1252, 1150, 825; $^1$H NMR (300 MHz, DMSO-d$_6$) δ2.15 (2H, m), 3.04 (2H, m), 3.34 (4H, m), 3.41 (2H, t, J=11.4 Hz), 3.74 (3H, s), 3.72 (2H, m), 4.15 (2H, t, J=6.0 Hz), 4.26 (2H, s), 5.45 (2H, brd s), 6.97 (2H, d, J=8.5 Hz), 7.18 (1H, dd, J=9.1 and 2.7 Hz), 7.36 (1H, d, J=2.7 Hz), 7.52 (2H, d, J=8.5 Hz), 7.57 (1H, s), 7.71 (1H, d, J=9.1 Hz), 11.14 (1H, s), 11.70 (1H, brd s); $^{13}$C NMR (75 MHZ, DMSO-d$_6$) δ22.97, 42.07, 45.97, 49.96, 55.25, 57.93, 65.70, 107.59, 110.26, 114.36, 118.32, 121.16, 125.38, 126.31, 127.24, 132.99, 136.80, 145.09, 154.61, 155.23, 160.07; MS m/e 512 (MH+).

Anal. Calcd. for C$_{25}$H$_{29}$N$_5$O$_5$S. 2HCl:
C, 51.37; H, 5.34; N, 11.98.
Found: C, 51.12; H, 5.59; N, 11.43.

EXAMPLE 18

1-[[3-(2,3-Dihydro-2-oxo-1H-imidazo-[4,5-b]quinolin-7-yl)oxy]propyl]sulfonyl]-4-(2-ethylbut-1-yl)piperazine dihydrochloride (10f)

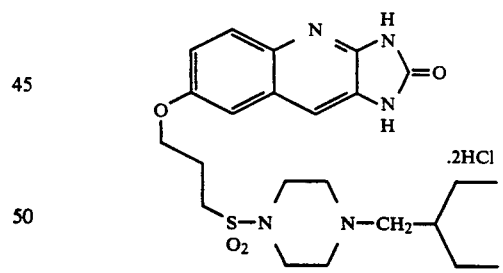

mp 273°-275° C.; IR (KBr, cm$^{-1}$) 3600-2300, 1730, 1624, 1372, 1328, 1236, 1140; $^1$H NMR (300 MHz, DMSO-d$_6$) δ0.81 (6H, t, J=7.3 Hz), 1.37 (4H, m), 1.69 (1H, m), 2.17 (2H, m) 2.95 (2H, t, J=5.6 Hz), 3.05 (2H, m), 3.35 (2H, m), 3.55 (2H, m), 3.66 (4H, m), 4.16 (2H, t, J=5.9 Hz), 7.23 (1H, dd, J=9.1 and 2.7 Hz), 7.41 (1H, d, J=2.7 Hz), 7.66 (1H, s), 7.79 (1H, d, J=9.1 Hz), 11.06 (1H, brd s), 11.35 (1H, s); $^{13}$C NMR (75 MHZ, DMSO-d$_6$) δ11.81, 24.65, 24.79, 36.26, 43.53, 47.56, 52.82, 60.87, 67.46, 109.46, 112.89, 120.42, 126.58, 127.40, 127.86, 136.82, 146.30, 156.55, 156.71; MS m/e 476 (MH+).

Anal. Calcd. for C$_{23}$H$_{33}$N$_5$O$_4$S. 2HCl. 0.7 H$_2$O:
C, 49.22; H, 6.54; N, 12.48.
Found: C, 49.22; H, 6.66; N, 12.54.

EXAMPLE 19

1-(Benzothiazol-2-yl)-4-[[3-[(2,3-dihydro-2-oxo-1H-imidazo[4,5-b]quinolin-7-yl)oxy]propyl]sulfonyl]piperazine hydrochloride (10i)

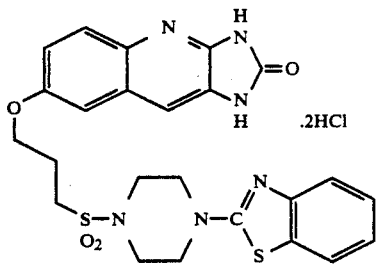

mp 345°-348° C.; IR (KBr, cm$^{-1}$) 3600-2700, 1722, 1344, 1238, 1146, 824, 756; $^1$H NMR (300 MHz, DMSO-d$_6$) δ2.17 (2H, m) 3.29 (2H, t, J=7.4 Hz), 3.37 (4H, m), 3.69 (4H, m), 4.14 (2H, t, J=5.9 Hz), 5.46 (2H, brd s), 7.10 (1H, t, J=7.8 Hz), 7.17 (1H, dd, J=9.1 and 2.7 Hz), 7.30 (1H, t, J=7.8 Hz), 7.34 (1H, d, J=2.7 Hz), 7.48 (1H, d, J=7.8 Hz), 7.55 (1H, s), 7.68 (1H, d, J=9.1 Hz), 7.79 (1H, d, J=7.8 Hz), 11.09 (1H, s), 11.5 (1H, brd s); $^{13}$C NMR (75 MHZ, DMSO-d$_6$) δ22.94, 44.53, 43.52, 48.15, 65.79, 107.58, 110.11, 118.28, 118.38, 121.51, 121.88, 125.33, 126.29, 127.37, 129.78, 136.99, 145.15, 150.92, 154.61, 155.26, 167.98, MS m/e 525 (MH+).

Anal. Calcd. for C$_{24}$H$_{24}$N$_6$O$_4$S$_2$. HCl.0.61 H$_2$O:
C, 50.28; H, 4.63; N, 14.66.
Found: C, 50.28; H, 4.64; N, 14.66.

What is claimed is:

1. A compound of the formula

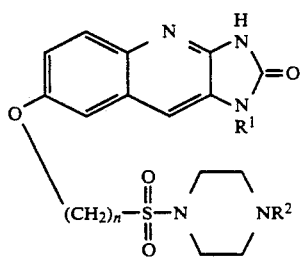

wherein
R$^1$ is H, or C$_1$-C$_4$ lower alkyl;
R$^2$ is H, (CH$_2$)$_m$R$^3$; benzoxazol-2yl, or benzothiazol-2-yl;
R$^3$ is C$_1$-C$_8$ alkyl, C$_4$-C$_8$ cycloalkyl, or substituted or unsubstituted phenyl, wherein the substituents are halogen, alkoxy or trifluoromethyl;
m is an integer of 1-3; and
n is an integer of 1-5;
or pharmaceutically acceptable salt thereof.

2. The intermediate compound which is 4-[[3-[(2,3-dihydro-2-oxo-1H-imidazo[4,5-b]quinolin-7-yl)oxy]propyl]sulfonyl]-1-piperazinecarboxaldehyde.

3. The compound of claim 1 which is 1-[[3-[(2,3-dihydro-2-oxo-1H-imidazo[4,5-b]quinolin-7-yl)oxy]propyl]sulfonyl]-1-piperazine or pharmaceutically acceptably salt thereof.

4. The compound of claim 1 which is 1-[[3-[(2,3-dihydro-2-oxo-1H-imidazo[4,5-b]quinolin-7-yl)oxy]propyl]sulfonyl]piperazine or pharmaceutically acceptable salt thereof.

5. The compound of claim 1 which is 1-[[3-[(2,3-dihydro-2-oxo-1H-imidazo[4,5-b]quinolin-7-yl)oxy]propyl]sulfonyl]-4-(2-phenylethyl)piperazine or pharmaceutically acceptable salt thereof.

6. The compound of claim 1 which is 1-[[3-[(2,3-dihydro-2-oxo-1H-imidazo[4,5-b]quinolin-7-yl)oxy]propyl]sulfonyl]-4-(phenylmethyl)piperazine or pharmaceutically acceptable salt thereof.

7. The compound of claim 1 which is 1-[[3-[(2,3-dihydro-2-oxo-1H-imidazo[4,5-b]quinolin-7-yl)oxy]propyl]sulfonyl]-4-(4-fluorophenylmethyl)piperazine or pharmaceutically acceptable salt thereof.

8. The compound of claim 1 which is 1-[[3-[(2,3-dihydro-2-oxo-1H-imidazo[4,5-b]quinolin-7-yl)oxy]propyl]sulfonyl]-4-(4-chlorophenylmethyl)piperazine or pharmaceutically acceptable salt thereof.

9. The compound of claim 1 which is 1-[[3-[(2,3-dihydro-2-oxo-1H-imidazo[4,5-b]quinolin-7-yl)oxy]propyl]sulfonyl]-4-(cyclohexylmethyl)piperazine or pharmaceutically acceptable salt thereof.

10. The compound of claim 1 which is 1-[[3-[(2,3-dihydro-2-oxo-1H-imidazo[4,5-b]quinolin-7-yl)oxy]propyl]sulfonyl]-4-(2-cyclohexylethyl)piperazine or pharmaceutically acceptable salt thereof.

11. The compound of claim 1 which is 1-[[3-[(2,3-dihydro-2-oxo-1H-imidazo[4,5-b]quinolin-7-yl)oxy]propyl]sulfonyl]-4-[(3-trifluoromethylphenyl)methyl]piperazine or pharmaceutically acceptable salt thereof.

12. The compound of claim 1 which is 1-(benzoxazol-2-yl)-4-[[3-[(2,3-dihydro-2-oxo-1H-imidazo[4,5-b]quinolin-7-yl)oxy]propyl]sulfonyl]piperazine or pharmaceutically acceptable salt thereof.

13. The compound of claim 1 which is 1-[[3-[(2,3-dihydro-2-oxo-1H-imidazo[4,5-b]quinolin-7-yl)oxy]propyl]sulfonyl]-4-[(4-methoxyphenylmethyl)piperazine or pharmaceutically acceptable salt thereof.

14. The compound of claim 1 which is 1-[[3-[(2,3-dihydro-2-oxo-1H-imidazo[4,5-b]quinolin-7-yl)oxy]propyl]sulfonyl]-4-(2-ethylbut-1-yl)piperazine or pharmaceutically acceptable salt thereof.

15. The compound of claim 1 which is 1-(benzothiazol-2-yl)-4-[[3-[(2,3-dihydro-2-oxo-1H -imidazo[4,5-b]quinolin-7-yl)oxy]propyl]sulfonyl]piperazine or pharmaceutically acceptable salt thereof.

16. A method for inhibiting blood platelet aggregation in a mammal which comprises administering a therapeutically effective amount of a compound of claim 1 or a pharmaceutically acceptable salt thereof.

17. The pharmaceutical composition for inhibiting blood platelet aggregation comprising a therapeutically effective amount of a compound of claim 1 or a pharmaceutically acceptable acid addition salt thereof and one or more pharmaceutical carriers.

* * * * *